US00PP37168P2

(12) United States Plant Patent
Capo

(10) Patent No.: US PP37,168 P2
(45) Date of Patent: Dec. 23, 2025

(54) ***PETUNIA* PLANT NAMED 'KLEPH24743'**

(50) Latin Name: ***Petunia* x *atkinsiana* (syn. *P. x hybrida)***
Varietal Denomination: KLEPH24743

(71) Applicant: KLEMM + SOHN GMBH & CO. KG., Stuttgart (DE)

(72) Inventor: Antonella Capo, Latina (IT)

(73) Assignee: Klemm + Sohn GMBH & Co. KG, Stuttgart (DE)

( * ) Notice: Subject to any disclaimer, the term of this patent is extended or adjusted under 35 U.S.C. 154(b) by 0 days.

(21) Appl. No.: 19/268,712

(22) Filed: Jul. 14, 2025

(51) Int. Cl.
*A01H 6/82* (2018.01)
*A01H 5/02* (2018.01)

(52) U.S. Cl.
USPC ..... Plt./356.23

(58) Field of Classification Search
USPC ..... Plt./356.23
CPC ..... A01H 6/824; A01H 5/02
See application file for complete search history.

*Primary Examiner* — Keith O. Robinson
(74) *Attorney, Agent, or Firm* — Weatherly IP Solutions, LLC; Karen P. Bechtold; James Weatherly

(57) ABSTRACT

A new *Petunia* plant particularly distinguished by red flowers with darker red veins and a trailing plant habit, is disclosed.

1 Drawing Sheet

Genus and species: *Petunia* x *atkinsiana* (syn. *P.* x *hybrida*).

Variety denomination: 'KLEPH24743'.

BACKGROUND OF THE NEW PLANT

The present invention comprises a new and distinct variety of *Petunia*, botanically known as *Petunia* x *atkinsiana* (syn. *P.* x *hybrida*) and hereinafter referred to by the variety name 'KLEPH24743'. 'KLEPH24743' is a selection from a controlled cross between the proprietary female *Petunia* line 'Easy Wave F1 Red Impr.' (not patented) and the male *Petunia* line 'Surfinia Red Trailing 2018' (not patented).

In July of 2019, the proprietary female *Petunia* line 'Easy Wave F1 Red Impr.' and the proprietary male *Petunia* line 'Surfinia Red Trailing 2018' were cross pollinated in Latina, Italy and seeds were obtained. The seeds were sown and plants were grown for evaluation. A plant line was selected in April 2020 in Latina, Italy and named 'KLEPH24743'. In May 2020, 'KLEPH24743' was first vegetatively propagated by terminal tip cuttings and tissue culture in Latina, Italy. 'KLEPH24743' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Red flowers with darker red veins; and
2. Trailing plant habit.

DESCRIPTION OF THE PHOTOGRAPH

This new *Petunia* plant is illustrated by the accompanying photograph, which shows a close-up of the flower of the plant. The plant is about ten weeks old grown in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLEPH24743'. The data which define these characteristics were collected from asexual reproductions carried out in Latina, Italy. Data was collected on thirteen-week-old plants grown indoors in Latina, Italy under greenhouse conditions in May 2025. Color references are to The R.H.S. Colour Chart of The Royal Horticultural Society of London (R.H.S.), 5$^{th}$ edition (2007).

Classification:

*Family.*—Solanaceae.
*Species.*—*Petunia* x *atkinsiana* (syn. *P.* x *hybrida*).
*Common name.*—*Petunia.*
*Variety.*—'KLEPH24743'.

Parentage:

*Female parent.*—'Easy Wave F1 Red Impr.' (not patented).
*Male parent.*—'Surfinia Red Trailing 2018' (not patented).

Plant:

*Form and habit.*—Medium to high vigor, trailing habit.
*Height (from top of soil).*—18.0 cm.
*Width (horizontal plant diameter).*—70.0 cm.
*Propagation type.*—Vegetative by terminal tip cuttings and tissue culture.
*Time to produce a finished flowering plant.*—About 12.5 weeks in winter under short day conditions, about 7 weeks in spring.
*Time to initiate and develop roots.*—2 to 3 weeks.
*Root description.*—Moderate density, moderate branching, white roots (RHS 155C).

Stems:

*Average number* (*basal*).—6.

*Length of basal branches* (*from the base of the stem to the tip*).—47.0 cm.

*Internode length*.—2.5 cm.

*Diameter of branches* (*from midpoint*).—0.35 cm.

*Stem color*.—RHS 144A.

*Anthocyanin*.—Absent.

*Texture*.—Pubescent.

Leaves:

*Arrangement*.—Alternate along the stem and opposite under the inflorescence.

*Length*.—6.5 cm.

*Width*.—4.5 cm.

*Shape*.—Ovate.

*Apex*.—Slightly obtuse.

*Base*.—Attenuate.

*Margin*.—Entire.

*Immature leaf color*.—Upper surface: RHS 138A. Lower surface: RHS 138B.

*Mature leaf color*.—Upper surface: RHS 137B. Lower surface: RHS 138B.

*Texture*.—Upper surface: Pubescent. Lower surface: Pubescent.

*Venation pattern*.—Arcuate.

*Venation color*.—Upper surface: RHS 137B. Lower surface: RHS 147C.

*Petioles*.—Length: 0.5 cm. Diameter: 0.35 cm. Color: RHS 144B. Texture: Pubescent.

Flower bud:

*Shape*.—Irregularly oblong.

*Length*.—4.5 cm.

*Diameter*.—0.7 cm.

*Color at tight bud*.—RHS 59A.

*Texture*.—Pubescent.

Inflorescence:

*Blooming habit* (*flowering season*).—Continuously flowering during spring and summertime.

*Inflorescence type*.—Sympodial, with monochasial growth.

*Number of flowers per node*.—1.

*Lastingness of individual blooms on the plant*.—About one week.

*Fragrance*.—Absent.

*Flowers*.—Arrangement: Composed of 5 petals, fused at the base. Diameter (flower face): 6.4 cm. Depth (total length of flower): 6.0 cm. Throat/Funnel: Length: 2.8 cm. Diameter (at opening): 1.5 cm. Texture: Inner surface: Smooth. Outer surface: Pubescent. Color: Inner surface: RHS 84C with veins RHS N92. Outer surface: RHS 76B. Petals: Color, mature flower (fully opened): Upper surface: RHS 42A. Lower surface: RHS 51B. Apex: Cuspidate. Base: Fused. Shape: Funnelform. Margin: Entire. Strength of waviness: Weak. Degree of lobation: Medium.

*Calyx arrangement*.—5 sepals fused at the base.

*Sepals*.—Color: Upper surface: RHS N137D. Lower surface: RHS 137B. Length: 1.6 cm. Width: 0.25 cm. Shape: Linear. Apex: Rounded. Base: Attenuate. Margin: Entire. Texture: Upper surface: Pubescent. Lower surface: Pubescent.

*Pedicels*.—Color: RHS 144A. Length: 2.0 cm. Diameter: 0.15 cm. Texture: Pubescent.

Reproductive organs:

*Stamens*.—Quantity: 5. Shape: Needle with oblong head. Filament: Length: From 1.1 cm to 1.4 cm. Diameter: 0.01 cm. Color: RHS 157B. Anther: Shape: Oblong. Color: RHS 156D. Length: 0.25 cm. Diameter: 0.2 cm. Pollen: Color: RHS 156A. Amount: Moderate.

*Pistils*.—Quantity per flower: 1. Length: 2.4 cm. Stigma color: RHS 193B. Style color: RHS 193A.

Fruit and seed set: None observed.

Disease and pest/insect resistance: None observed.

COMPARISON WITH PARENTAL LINES AND KNOWN VARIETY

'KLEPH24743' is a distinct variety of *Petunia*. 'KLEPH24743' is distinguished from its parents as described in Table 1:

TABLE 1

Comparison with Parental Lines

| Characteristic | Subject Variety 'KLEPH24743' | Female parent *Petunia* 'Easy Wave F1 Red Impr.' | Male Parent *Petunia* 'Surfinia Red Trailing 2018' |
|---|---|---|---|
| Flower color | Red | Darker red | Red |
| Growth habit | Trailing | Semi-upright | Very flat |

'KLEPH24743' is most similar to the commercial *Petunia* plant named 'KLEPH14248' (U.S. Plant Pat. No. 27,046). Differences between the two varieties are described in Table 2:

TABLE 2

Comparison with Similar Variety

| Characteristic | Subject Variety 'KLEPH24743' | Commercial line 'KLEPH14248' (U.S. Plant Pat. No. 27,046) |
|---|---|---|
| Growth | Medium-high vigor, trailing | More compact, semi-trailing |

I claim:

1. A new and distinct variety of *Petunia* plant named 'KLEPH24743' as shown and described herein.

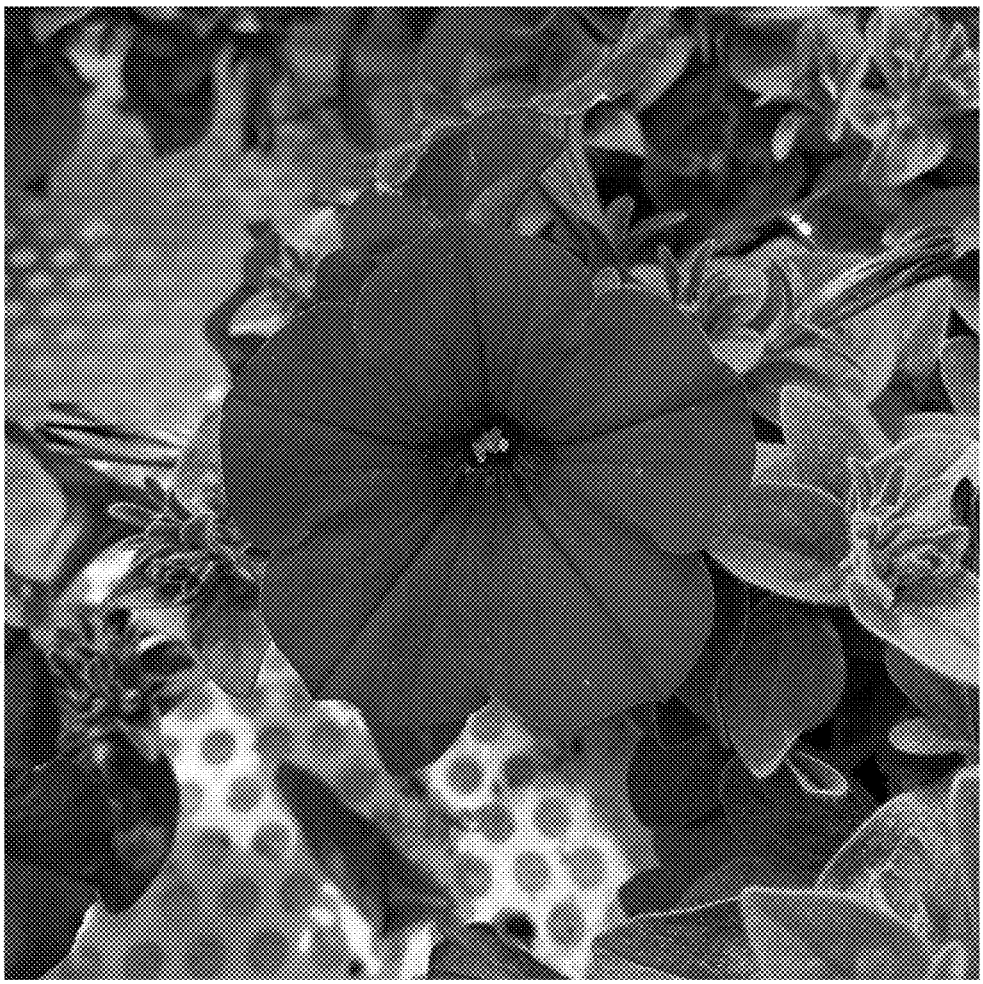

* * * * *